(12) United States Patent
Nabutovsky et al.

(10) Patent No.: US 9,980,665 B2
(45) Date of Patent: *May 29, 2018

(54) METHODS AND SYSTEMS TO CALCULATE TIME OF MECHANICAL ACTIVATION USING CHARACTERIZATION MOTION DATA AREA STRAINS

(71) Applicant: Pacesetter, Inc., Sunnyvale, CA (US)

(72) Inventors: Yelena Nabutovsky, Mountain View, CA (US); Hoda Razavi, San Jose, CA (US)

(73) Assignee: Pacesetter, Inc., Sunnyvale, CA (US)

(*) Notice: Subject to any disclaimer, the term of this patent is extended or adjusted under 35 U.S.C. 154(b) by 463 days.

This patent is subject to a terminal disclaimer.

(21) Appl. No.: 14/703,764

(22) Filed: May 4, 2015

(65) Prior Publication Data

US 2015/0313482 A1 Nov. 5, 2015

Related U.S. Application Data

(60) Provisional application No. 61/988,779, filed on May 5, 2014.

(51) Int. Cl.
*G06F 15/00* (2006.01)
*G06F 15/18* (2006.01)
(Continued)

(52) U.S. Cl.
CPC ............ *A61B 5/11* (2013.01); *A61B 5/02028* (2013.01); *A61B 5/042* (2013.01); *A61B 5/04012* (2013.01); *A61B 5/0452* (2013.01); *A61B 5/062* (2013.01); *A61B 5/1107* (2013.01); *A61B 5/7278* (2013.01); *A61B 5/742* (2013.01);
(Continued)

(58) Field of Classification Search
USPC .......................................................... 706/62
See application file for complete search history.

(56) References Cited

U.S. PATENT DOCUMENTS 7,197,354 B2  3/2007  Sobe
7,881,769 B2  2/2011  Sobe
(Continued)

OTHER PUBLICATIONS

Stent Maps—Comparative Visualization for the Prediction of Adverse Events of Transcatheter Aortic Valve Implantations Silvia Born; Simon H. Sündermann; Christoph Russ; Raoul Hopf; Carlos E. Ruiz; Volkmar Falk; Michael Gessat IEEE Transactions on Visualization and Computer Graphics Year: 2014, vol. 20, Issue: 12 pp. 2704-2713 IEEE.*

(Continued)

*Primary Examiner* — Michael B Holmes
(74) *Attorney, Agent, or Firm* — Theresa A. Raymer

(57) ABSTRACT

A method and system is provided for determining the mechanical activation of a region of interest. The system and method include using a triangulation technique algorithm to generate at least one triangle within a region of interest, wherein the triangle is formed from map points acquired from an intravascular mapping tool. The system and method further include calculating an area strain for each triangle, determining abnormal areas of the region of interest, and excluding triangles that include the abnormal area. Further, the system and method include determining a mechanical activation time for the region of interest based on the remaining triangles.

14 Claims, 10 Drawing Sheets

(51) Int. Cl.
| | |
|---|---|
| *A61B 5/11* | (2006.01) |
| *A61B 5/02* | (2006.01) |
| *A61B 5/04* | (2006.01) |
| *A61B 5/00* | (2006.01) |
| *A61B 5/0452* | (2006.01) |
| *A61B 5/042* | (2006.01) |
| *A61B 5/06* | (2006.01) |
| *A61B 6/12* | (2006.01) |
| *A61B 6/00* | (2006.01) |

(52) U.S. Cl.
CPC ............... *A61B 6/12* (2013.01); *A61B 6/4441* (2013.01); *A61B 6/487* (2013.01); *A61B 6/503* (2013.01); *A61B 6/504* (2013.01); *A61B 6/5247* (2013.01)

(56) References Cited

U.S. PATENT DOCUMENTS

| | | | | |
|---|---|---|---|---|
| 8,016,764 | B1 | 9/2011 | Shelchuk | |
| 9,314,191 | B2 * | 4/2016 | Razavi | A61B 5/1107 |
| 9,314,300 | B2 * | 4/2016 | Nabutovsky | A61B 18/1492 |
| 9,333,351 | B2 * | 5/2016 | Arnold | A61N 1/3611 |
| 9,345,550 | B2 * | 5/2016 | Richter | A61B 34/10 |
| 9,364,170 | B2 * | 6/2016 | Nabutovsky | A61B 5/1126 |
| 9,380,940 | B2 * | 7/2016 | Razavi | A61B 5/0044 |
| 9,427,283 | B2 * | 8/2016 | Nabutovsky | A61B 18/18 |
| 9,427,594 | B1 * | 8/2016 | Bornzin | A61B 5/6852 |
| 9,427,595 | B2 * | 8/2016 | Nabutovsky | A61N 1/36017 |
| 9,462,959 | B2 * | 10/2016 | Nabutovsky | A61B 5/021 |
| 9,561,376 | B2 * | 2/2017 | Qu | A61N 1/3686 |
| 9,700,233 | B2 * | 7/2017 | Razavi | A61B 5/062 |
| 9,713,494 | B2 * | 7/2017 | Nabutovsky | A61B 18/1492 |
| 9,763,591 | B2 * | 9/2017 | Nabutovsky | A61B 5/044 |
| 9,814,406 | B2 * | 11/2017 | Razavi | A61B 5/0468 |
| 9,861,823 | B2 * | 1/2018 | Nabutovsky | A61N 1/3684 |
| 2013/0272592 | A1 | 10/2013 | Eichler et al. | |

OTHER PUBLICATIONS

Cooperative sensor anomaly detection using global information Rui Zhang; Ping Ji; Dinkar Mylaraswamy; Mani Srivastava; Sadaf Zahedi Tsinghua Science and Technology Year: 2013, vol. 18, Issue: 3 pp. 209-219 TUP Journals & Magazines.*

Geometric spherical networks for Visual Data processing E. Castillo-Muñiz; E. Bayro-Corrochano The 2012 International Joint Conference on Neural Networks (IJCNN) Year: 2012 pp. 1-8 IEEE Conference Publications.*

Geometrically accurate activation mapping of the atrioventricular node region during surgery; Richard C.Saumarez PhD, MRCP, JohnParker FRCS, FRCP, JohnCamm MD, FRCP, FACC London, England Received Apr. 30, 1991, Revised Aug. 12, 1991, Accepted Aug. 23, 1991, Available online May 30, 2010.*

A Methodology for Automated Segmentation and Reconstruction of Urban 3-D Buildings from ALS Point Clouds Dong Chen; Liqiang Zhang; P. Takis Mathiopoulos; Xianfeng Huang IEEE Journal of Selected Topics in Applied Earth Observations and Remote Sensing Year: 2014, vol. 7, Issue: 10 pp. 4199-4217 IEEE Journals & Magazines.*

RGBD Point Cloud Alignment Using Lucas-Kanade Data Association and Automatic Error Metric Selection Brian Peasley; Stan Birchfield IEEE Transactions on Robotics Year: 2015, vol. 31, Issue: 6 pp. 1548-1554 IEEE Journals & Magazines.*

What should I landmark? Entropy of normals in depth juts for place recognition in changing environments using RGB-D data Daniel Gutiérrez-Gómez; Walterio Mayol-Cuevas; J. J. Guerrero 2015 IEEE International Conference on Robotics and Automation (ICRA) Year: 2015 pp. 5468-5474 IEEE Conferences.*

Detection of 3-D Individual Trees in Urban Areas by Combining Airborne LiDAR Data and Imagery Wei Yao; Yuzhang Wei IEEE Geoscience and Remote Sensing Letters Year: 2013, vol. 10, Issue: 6 pp. 1355-1359 IEEE Journals & Magazines.*

* cited by examiner

METHODS AND SYSTEMS TO CALCULATE TIME OF MECHANICAL ACTIVATION USING CHARACTERIZATION MOTION DATA AREA STRAINS

RELATED APPLICATION DATA

The present application relates to and claims priority from the following application: U.S. provisional application Ser. No. 61/988,779, filed May 5, 2014, titled "METHODS AND SYSTEMS TO CALCULATE TIME OF MECHANICAL ACTIVATION USING CHARACTERIZATION MOTION DATA AREA STRAINS" which is expressly incorporated herein by reference in their entirety in the present application.

BACKGROUND OF THE INVENTION

Embodiments of the present disclosure generally relate to methods and systems for cardiovascular navigation, and more particularly for calculating the strain from characterization data of a cardiac chamber or organ.

Cardiovascular navigation systems (CNS) provide real-time position and orientation information in relation to a part of the cardiovascular system, such as, the heart based on sensors placed at various locations within the cardiovascular system. The CNS may be integrated with a fluoroscopic (or other diagnostic) imaging system and track the sensors continuously within an imaging volume defined by the fluoroscopic system, on both live and recorded background diagnostic images.

Recently, it has been proposed to utilize the CNS to evaluate the motion of the heart and identify a desired (e.g., optimal) location for placement of a left ventricular (LV) lead. For example, the CNS may systematically record information, such as displacement of the sensors, associated with various endocardial and epicardial locations of the LV. Epicardial locations may include mapping within the coronary sinus branches as well as mapping directly on the epicardial surface of the LV via a sub-xiphoid puncture technique, for example. Depending on the size of the heart and other factors during the procedure, there may be between 40 and 120 endocardial LV locations and up to 10 epicardial locations at which the MDG system obtains recordings for each patient.

Systems have been proposed to characterize the motion of the heart, specifically on the qualitative techniques of characterizing motion. However, the systems proposed thus far do not offer sufficient information to prepare acquired characterization data for strain analysis. A need remains for methods and system that can offer more information about calculating strain from characterization data.

SUMMARY

In accordance with an embodiment herein, a method is provided for determining the mechanical activation of a region of interest. The method includes using a triangulation technique algorithm to generate at least one triangle within a region of interest, wherein the triangle is formed from map points acquired from an intravascular mapping tool. The method further includes calculating an area strain for each triangle, determining abnormal areas of the region of interest, and excluding triangles that include the abnormal area. Further, the method includes determining a mechanical activation time for the region of interest based on the remaining triangles.

DETAILED DESCRIPTION

Figure 1:
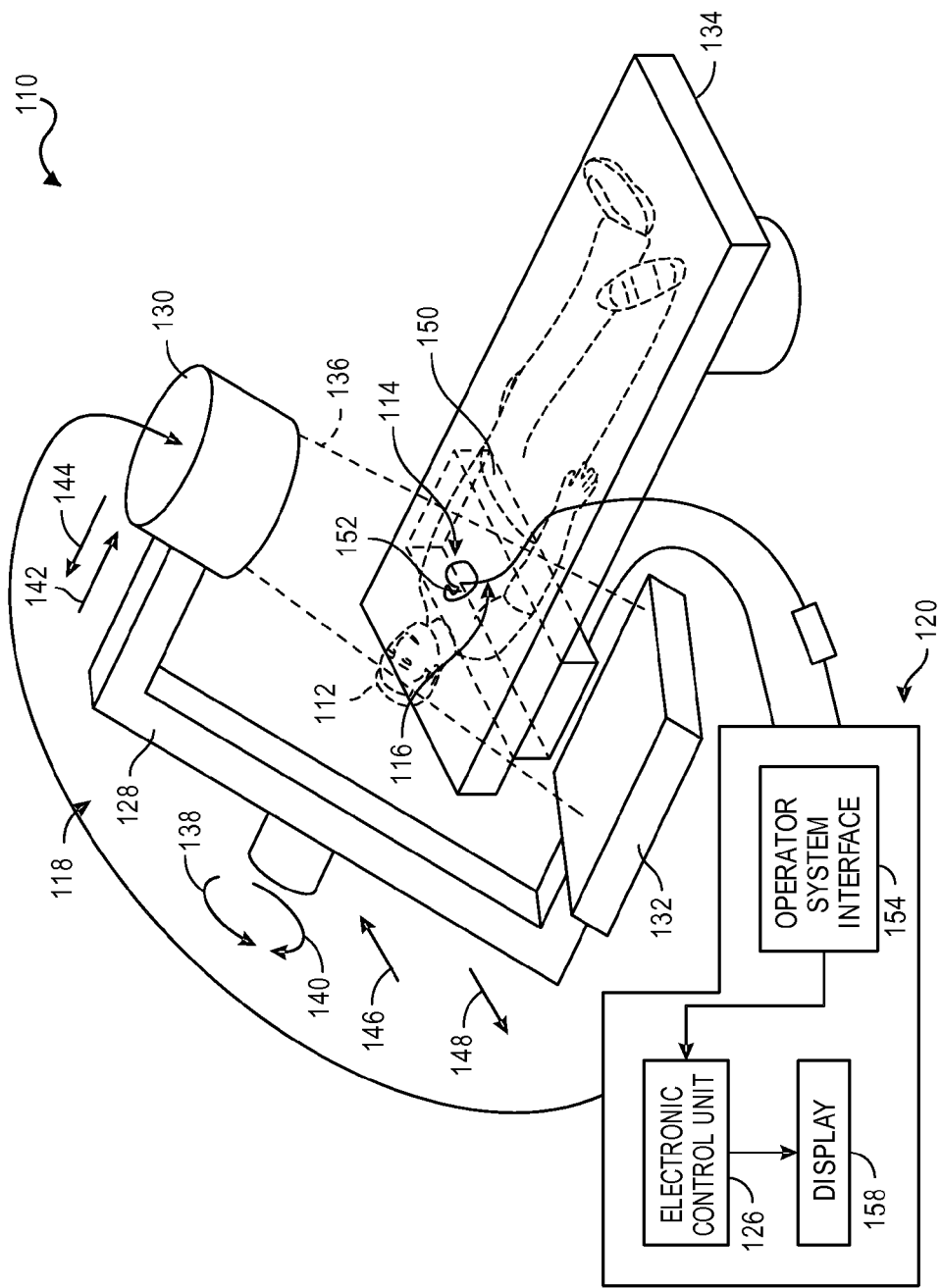
FIG. 1 illustrates a cardiovascular navigation system for use in imaging an anatomical region of the heart and to collect motion data, in accordance an embodiment herein.

Embodiments herein may be implemented with, and/or utilize aspects of, the methods and system described in the following applications:

- U.S. patent application Ser. No. 14/328,523, filed Jul. 10, 2014, titled "METHOD AND SYSTEM TO ASSESS MECHANICAL DYSSYNCHRONY BASED ON MOTION DATA COLLECTED BY A NAVIGATION SYSTEM",
- U.S. patent application Ser. No. 14/328,523, filed Jul. 10, 2014, titled "METHOD AND SYSTEM TO MEASURE CARDIAC MOTION USING A CARDIOVASCULAR NAVIGATION SYSTEM",
- U.S. patent application Ser. No. 14/478,707, filed Sep. 5, 2014, titled "METHOD AND SYSTEM TO IDENTIFY MOTION DATA ASSOCIATED WITH CONSISTENT ELECTRICAL AND MECHANICAL BEHAVIOR FOR A REGION OF INTEREST",
- U.S. patent application Ser. No. 14/270,181, filed May 5, 2014, titled "METHOD AND SYSTEM TO CHARACTERIZE MOTION DATA BASED ON NEIGHBORING MAP POINTS",
- U.S. patent application Ser. No. 14/270,186, filed May 5, 2014, titled "METHOD AND SYSTEM FOR CACLULATING STRAIN FROM CHARACTERIZATION DATA OF A CARDIAC CHAMBER",
- U.S. patent application Ser. No. 14/270,176, filed May 5, 2014, titled "METHOD AND SYSTEM FOR DISPLAYING A THREE DIMENSIONAL VISUALIZATION OF CARDIAC MOTION",
- U.S. patent application 61/988,735, filed May 5, 2014, titled "METHOD AND SYSTEM TO DETERMINE

CARDIAC CYCLE LENGTH IN CONNECTION WITH CARDIAC MAPPING",

U.S. patent application 61/988,763, filed May 5, 2014, titled "METHOD AND SYSTEM TO EQUALIZING CARDIAC CYCLE LENGTH BETWEEN MAP POINTS", U.S. patent application 61/988,767, filed May 5, 2014, titled "METHOD AND SYSTEM TO SUBDIVIDE A MAPPING AREA FOR MECHANICAL ACTIVATION ANALYSIS", U.S. patent application 61/988,771, filed May 5, 2014, titled "CARDIAC RESYNCHRONIZATION SYSTEM AND METHOD" having docket number A14P3006, and U.S. patent application 61/988,774, filed May 5, 2014, titled "SYSTEM AND METHOD FOR EVALUATING LEAD STABILITY OF AN IMPLANTABLE MEDICAL DEVICE".

All of the above cited applications are expressly incorporated herein by reference in their entirety.

The description that follows sets forth one or more illustrative embodiments. It will be apparent that the teachings herein may be embodied in a wide variety of forms, some of which may appear to be quite different from those of the disclosed embodiments. Consequently, the specific structural and functional details disclosed herein are merely representative and do not limit the scope of the disclosure. For example, based on the teachings herein one skilled in the art should appreciate that the various structural and functional details disclosed herein may be incorporated in an embodiment independently of any other structural or functional details. Thus, an apparatus may be implemented or a method practiced using any number of the structural or functional details set forth in any disclosed embodiment(s). Also, an apparatus may be implemented or a method practiced using other structural or functional details in addition to or other than the structural or functional details set forth in any disclosed embodiment(s).

FIG. 1 illustrates a cardiovascular navigation system (CNS) 110, of an embodiment, for use in imaging an anatomical region of a patient 112, such as, a heart 114. A medical tool 116 is placed within the anatomical region, such as for example, an electrophysiological (EP) mapping catheter (e.g., a guidewire), or a catheter generally described or shown in U.S. Pat. No. 7,881,769, which is expressly incorporated herein by reference. The medical tool 116 includes a plurality of electrophysiological sensors 152 that may be placed on the endocardial or epicardial surface of the left ventricle (LV) of the heart 114. The electrophysiological sensors 152 may be attached to the distal or proximal end of the medical tool 116, or any point in between. The electrophysiological sensors 152 measure a position and an electrical potential or an electric current of biological cells and tissues. The electrophysiological sensors 152 transmit the position and electrical potential information to an electronic control unit (ECU) 126. For example, the electrophysiological sensors 152 may be positioned by the medical tool 116 to measure point specific (PS) motion data for a plurality of map points of the wall of the heart 114. It should be understood, however, that the electrophysiological sensors 152 could be used in a variety of anatomical regions or alternative map points within the heart 114 or other organs in which motion characterization may be of interest. Additionally or alternatively, the electrophysiological sensors 152 may be replaced by separate motion sensors and electrical sensors. The motion sensors in contact with the region of interest (e.g., the LV of the heart 114) measuring the position sensors as well as the electrical sensors that are measuring the PS motion data of the region of interest. Optionally, the ECU 126 may receive the PS motion data and electrical sensor measurements simultaneously from the motion sensors and electrical sensors.

A navigation system 120 is provided to determine the position and orientation of the medical tool 116 within the body of the patient 112. In the illustrated embodiment, the navigation system 120 comprises a magnetic navigation system in which magnetic fields are generated in the anatomical region and position sensors associated with the medical tool 116 generate an output that is responsive to the position of the sensors within the magnetic field. The navigation system 120 may comprise, for example, the systems generally shown and described in, for example, U.S. Pat. Nos. 6,233,476, 7,197,354, 7,386,339, and 7,505,809 all of which are expressly incorporated by reference in their entirety. Although a magnetic navigation system is shown in the illustrated embodiment, it should be understood that the embodiments could find use with a variety of navigation systems including those based on the creation and detection of axes specific electric fields. The navigation system 120 may include a transmitter assembly 150.

The transmitter assembly 150 may include a plurality of coils arranged orthogonally to one another to produce a magnetic field in and/or around the anatomical region of interest. It should be noted that, although the transmitter assembly 150 is shown under the body of the patient 112 and under the table 134 in FIG. 1, the transmitter assembly 150 may be placed in another location, such as, attached to the radiation emitter 130, from which the magnetic field generators can project a magnetic field in the anatomical region of interest. In accordance with certain embodiments the transmitter assembly 150 is within the field of view 136. The ECU 126 may control the generation of magnetic fields by transmitter assembly 150.

The electrophysiological sensors 152 are configured to generate an output dependent on the relative position of electrophysiological sensors 152 within the field generated by the transmitter assembly 150. In FIG. 1, the electrophysiological sensor 152 and the medical tool 116 are shown disposed around the heart 114. The navigation system 120 determines the location of the electrophysiological sensors 152 within the generated field, and thus the position of the medical tool 116 as well. The navigation system 120 may further determine navigation coordinates, such as a cartesian coordinate (e.g., (X, Y, Z)), of the navigation coordinate system.

The ECU 126 of the navigation system 120 may include or represent hardware circuits or circuitry that include and/or are connected with one or more logic based devices, such as processors, microprocessors, controllers, microcontrollers, or other logic based devices (and/or associated hardware, circuitry, and/or software stored on a tangible and non-transitory computer readable medium or memory). The ECU 126 may receive a plurality of input signals including signals generated by the medical tool 116, the electrophysiological sensors 152, an operator system interface 154 (e.g., keyboard, touchscreen, or the like), and one or more patient reference sensors (not shown) and generate a plurality of output signals including those used to control the medical tool 116 and/or the display 158. The ECU 126 may also receive an input signal from an organ monitor (not shown), such as an ECG monitor, and sort or segregate images from an imaging system 118 based on a timing signal of a monitored organ. For example, ECU 126 may sort images based on the phase of the patient's cardiac cycle at which each image was collected, as more fully described in U.S. Pat. No. 7,697,973, which is hereby incorporated by reference in its entirety.

Optionally, the CNS 110 may include an imaging system 118. The CNS 110 may further include a registration system for registering a group of images of the anatomical region of the patient 112 in a navigation coordinate system of the navigation system 120 as generally described and shown in U.S. Patent Publication 2013/0272592 and International Pub. No. WO 2012090148, the entire disclosure of which is expressly incorporated herein by reference.

The imaging system 118 may be provided to acquire images of the heart 114 or another anatomical region of interest. The imaging system 110 may, for example, comprise of a fluoroscopic imaging system. Additionally or alternatively, rather than a fluoroscopic imaging system, computed tomography (CT) imaging systems, a three-dimensional radio angiography (3DRA) system, SPECT, PET, X-ray, MR, ultrasound and the like may be used. Although the imaging system 118 is described herein for an exemplary embodiment of the invention, the imaging system 118 is not required for the inventive subject matter described within this application.

The imaging system 118 may include a C-arm support structure 128, a radiation emitter 130, and a radiation detector 132. The emitter 130 and detector 132 are disposed on opposite ends of the support structure 128 and disposed on opposite sides of the patient 112 as the patient 112 lays on an operation table 134. The emitter 130 and detector 132 define a field of view 136 and are positioned such that the field of view 136 includes the anatomical region of interest as the patient 112 lays on the operation table 134. The imaging system 118 is configured to capture images of anatomical features and other objects within the field of view 136. The support structure 128 may have freedom to rotate about the patient 112 as shown by lines 138 and 140. The support structure 128 may also have freedom to slide along lines 142 and 144 (e.g., along the cranio-caudal axis of the patient 112) and/or along lines 146 and 148 (e.g., perpendicular to the cranio-caudal axis of the patient 112). Rotational and translational movement of the support structure 128 yields corresponding rotational and translational movement of the field of view 136. Additionally or alternatively, the navigation system 120 may adjust the navigation coordinates of the position of the medical tool 116 to compensate for changes in the C-arm support structure 128 and respiratory movements of the patient as disclosed in the U.S. Provisional Application No. 61/910,630, entitled, "METHOD TO MEASURE CARDIAC MOTION USING A CARDIOVASCULAR NAVIGATION SYSTEM," which is expressly incorporated herein by reference in its entirety.

The imaging system 118 may acquire a group of images of an anatomical region of the patient 112 by first shifting along lines 142, 144, 146, and/or 148 to place the anatomical region of interest within the field of view 136. Second, the support structure 128 may rotate the radiation emitter 130 and the radiation detector 132 about the patient 112, keeping the anatomical region within the field of view 136. The imaging system 118 may capture images of the anatomical region as the support structure 128 rotates, providing a group of two-dimensional images of the anatomical region from a variety of angles. The group of images may be communicated to the ECU 126 for image processing and display. The group of images may comprise a sequence of images taken over a predetermined time period.

Additionally, one or more patient reference sensors (not shown) may be on the body of the patient 112, for example, on the chest. The patient reference sensors measure a displacement and orientation of the patient reference sensors relative to a predetermined reference point, such as, the electrophysiological sensors 152 or the transmitter assembly 150.

Figure 2:
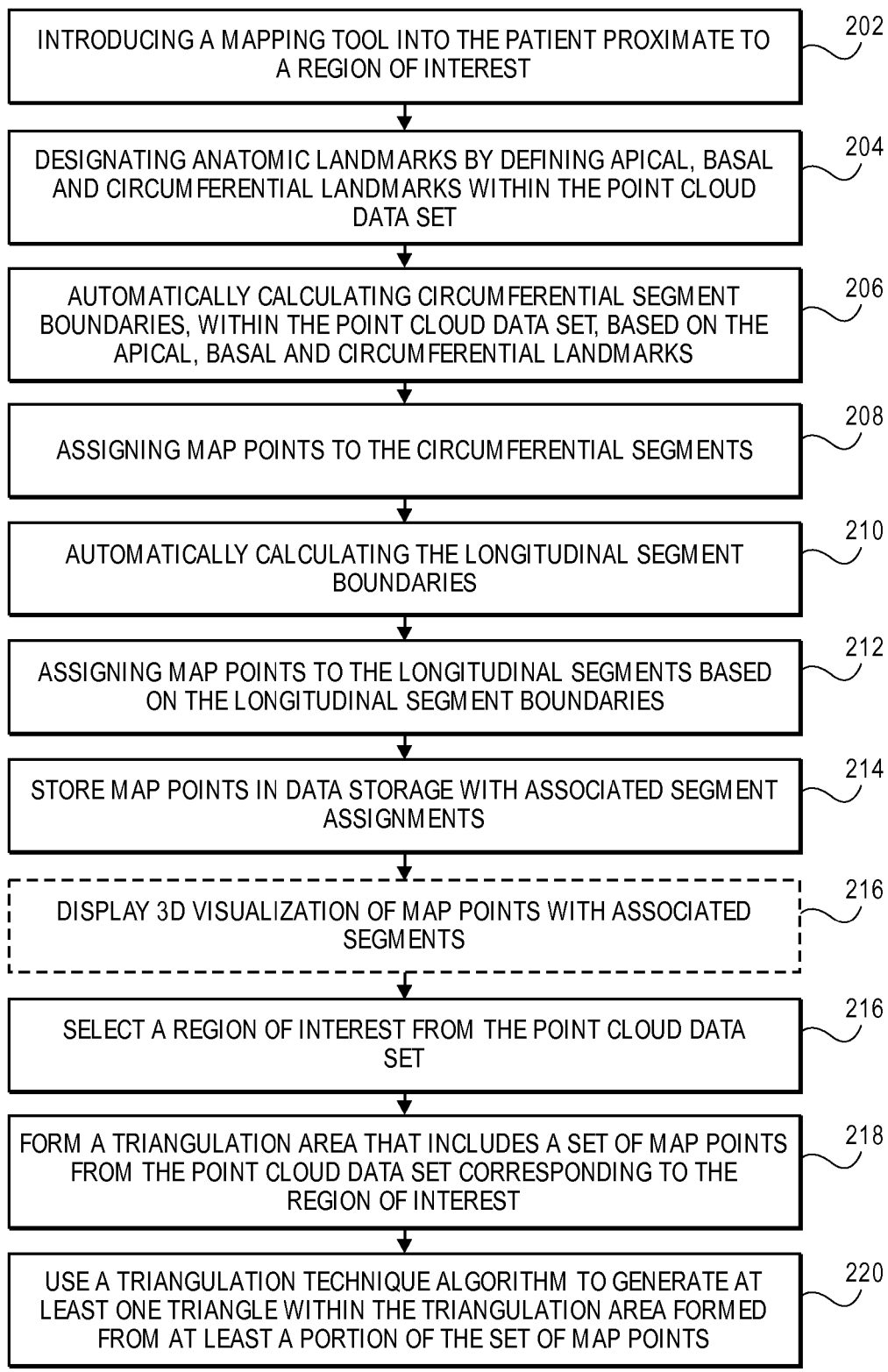
FIG. 2 illustrates a method performed in accordance with embodiments herein for assigning map points to anatomical segments of the heart.

FIG. 2 illustrates a method 200 performed in accordance with embodiments herein for assigning map points to anatomical segments of the heart and subdividing a region of interest into triangles. Throughout the present application, examples are provided in connection with mapping the left ventricle (LV). It should be recognized that the operations described herein may be used to map other regions of the heart. When mapping other regions of interest in the heart, different reference points and landmarks may be used.

Beginning at 202, a mapping tool (e.g., the medical tool 116) is introduced into the patient 112 proximate to a region of interest (e.g., the LV). Images are displayed to the user through the display 158. The images may be collected from various diagnostic imaging modalities (e.g. fluoroscopy, X-ray, MR, ultrasound, CT, PET, SPECT and the like) from the imaging system 118. Information from the navigation system 120, regarding the mapping tool, is combined with the images of the region of interest, and graphical representations are displayed of the mapping tool, in combination with the diagnostic image(s) on the display 158. For example, the mapping tool may be displayed superimposed upon the diagnostic image(s). By way of example, the physician may utilize intravascular mapping tool that is configured to be inserted proximate to the heart, endocardially and/or epicardially. The physician maneuvers the mapping tool between multiple locations of interest that are proximate to select areas on interior and/or exterior surfaces of the heart. For example, the physician may manipulate a mapping tool within the left ventricle and/or right ventricle to collect endocardial mapping data associated with interior surfaces of the chambers of the heart.

Additionally or alternatively, the physician may maneuver the mapping tool along one or more veins that extend about an exterior of a select region/chamber of the heart, such as the right ventricle and/or left ventricle, to collect epicardial mapping data. The medical tool may acquire point specific (PS) motion data of the heart at numerous map points positioned along the walls of the various chambers during at least one cardiac cycle.

Figure 3:
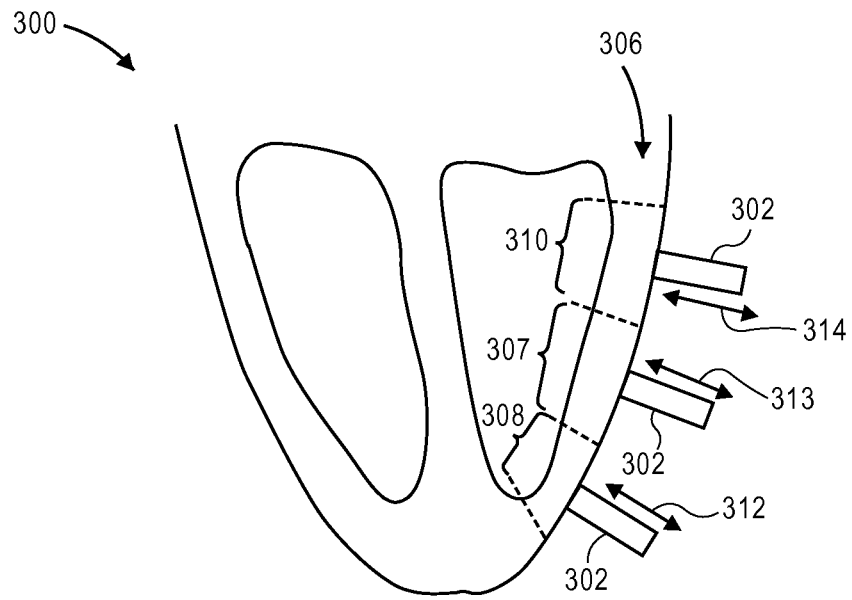
FIG. 3 illustrates a graphical representation of a plurality of map points of a heart.

FIG. 3 illustrates a graphical representation of a portion of a heart 300 with a medical tool 302 positioned to acquire PS motion data. For example, the medical tool 302 may be used to acquire PS motion data for a plurality of map points 308-310 associated with a heart wall 306. The PS motion data forms a portion of a point cloud data set. The point cloud data set may include all data collected by the medical tool 302, which may include information other than PS motion data. The term "point specific" is used to indicate that the motion data is associated with a single select location on the heart wall. The data values represent positions of the single select location over one or more cardiac cycles. The example of FIG. 3 shows three map points of interest 308-310 along the heart wall. Optionally, more or fewer map points of interest may be designated to expand the point cloud data set. The medical tool 302, which may correspond the medical tool 116 of FIG. 1 with the plurality of electrophysiology sensors 152, is positioned directly against the heart wall 306 at one or more points of interest 308-310. The tool 302 measures movement of the one or more points over a select period of time. In the example of FIG. 3, the tool 302 is shown positioned against map points 308-310 at different points in time.

For example, the tool 302 is positioned, during a first measuring operation, at the map point 308 while collecting PS motion data associated with movement (e.g., along the arrow 312) by the map point 308. The movement may be in various linear, transverse, or rotational directions. The map point data is continuously or periodically collected and added to data collection, generally referred to as the point cloud data set. Next, the tool 302 may be positioned, during a second measuring operation, at the map point 309 while collecting PS motion data associated with movement (e.g., along the arrow 313) by the map point 309. Next, the tool 302 is positioned, during a third measuring operation, at the map point 310 while collecting PS motion data associated with movement (e.g., along the arrow 314) by the map point 310. The position of the tool 302 may be continuously monitored by a navigation system (e.g., the navigation system 120) to obtain sets of PS motion data associated with each map point 308-310 over a select period of time, such as, during at least one cardiac cycle.

The point cloud data set expands over time thereby increasing an amount of information regarding the electrical and/or mechanical behavior of the region of interest within the heart. The point cloud data set is stored in a data storage (e.g., such as at a local terminal or workstation, a local area network, a wide area network, on a network, or at a remote data storage facility). By way of example, the data storage may be configured to store map point data collected by an intravascular mapping tool configured to be inserted into at least one of the endocardial or epicardial space. The mapping tool is maneuvered to select locations proximate to surfaces of the heart, while collecting the map point data at map points to form a point cloud data set during at least one cardiac cycle, the map point data represents at least one of motion or electrical activity data at the map points.

As explained herein, various analyses may be performed iteratively upon the point cloud data set throughout the data collection process. It is not necessary for a complete point cloud to be collected before analyzing the map point data.

Optionally, the navigation system 120 (FIG. 1) may perform pre-processing on the point cloud data set. For example, the CNS 110 may filter or remove PS motion data within the point cloud data set that was acquired during irregular or invalid beats (e.g., ectopic beats). The navigation system 120 may receive electrical sensor measurements of the patient 112 from a 12-lead surface electrocardiogram (ECG), body surface mapping (BSM), subcutaneous ECG, a uni- or bi-polar intracardiac electrograms (IEGMs) of a catheter, such as the medical tool 116, placed in the coronary sinus (CS), right ventricular (RV apex), or the like. The navigation system 120 may identify the invalid or irregular beats from the electrical sensor measurements and remove the invalid or irregular beats with the corresponding PS motion data subset acquired during the beat from the point cloud data set as disclosed in U.S. application Ser. No. 14/478,707.

Optionally, the navigation system 120 may adjust PS motion data within the point cloud data set based on motion waveforms. A motion waveform represents the motion of a map point during a cardiac cycle as defined by the PS motion data. For example, the PS motion data may be adjusted temporally equalized by "stretching" motion waveforms that have shorter cycle lengths until the shorter motion waveform subsets have a length equal to a predetermined or common time interval. The common time interval may be predetermined, or automatically selected, such as by choosing a length corresponding to the longest, shortest, or average length of the motion waveforms defined by the PS motion data within the point cloud data set. The time interval may be set to begin at a point in time defined by a global signal such as the peak of the R-wave as detected by using the Electrocardiogram (ECG) or Intracardiac Electrogram (IEGM) signals. Optionally, the time interval may be defined to begin based on another global marker of electrical activity (e.g., the T-wave, P-wave).

Additionally or alternatively, the navigation system 120 may apply a rotation technique to the motion waveform to correct for non-periodicity, such as the rotation techniques described in U.S. application Ser. No. 14/328,513. A periodic motion waveform of a map point during the cardiac cycle has, at the start and end of the cardiac cycle, approximately the same measured displacement or position. Non-periodicity may occur from errors in the acquired PS motion data for the map point that defines the motion waveform. For example, if the electrophysiological sensor 152 is not maintained directly against the heart wall during the entire cardiac cycle, the PS motion data may drift.

Figure 4:
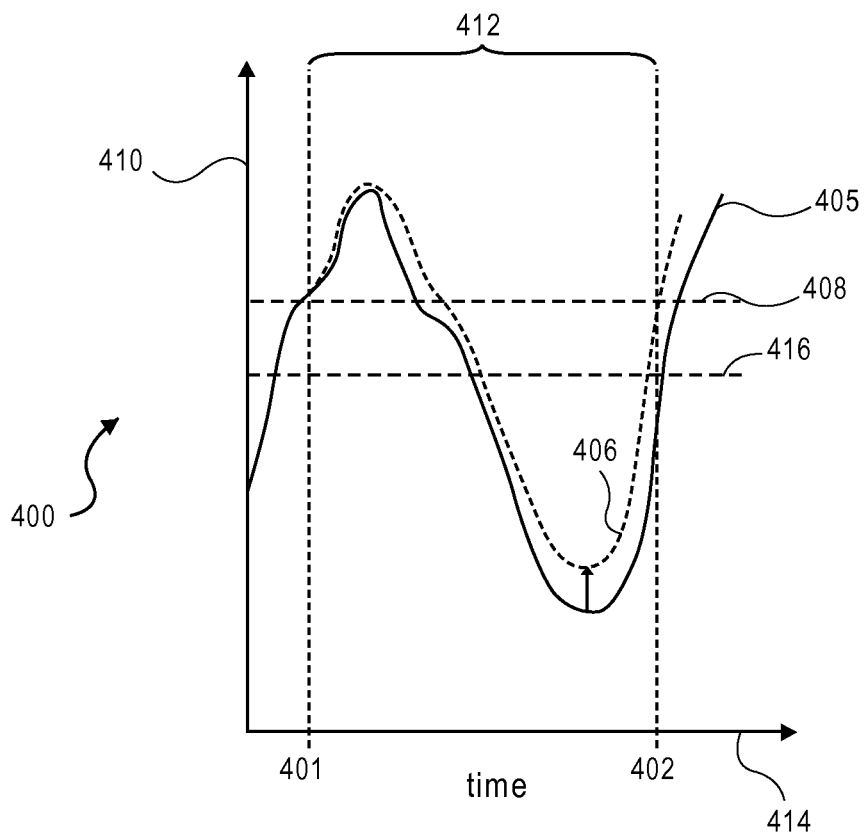
FIG. 4 illustrates a motion waveform associated with a map point being rotated in accordance with an embodiment herein.

FIG. 4 illustrates a graph 400 for a motion waveform 405 that is defined by a plurality of PS motion data associated with a select map point (e.g., the map point 308 in FIG. 3). The motion waveform 405 represents a displacement of the map point with respect to a vertical axis 410 over time as denoted along a horizontal axis 414. A cardiac cycle 412 is represented between start 401 and end 402. At the start 401 of the cardiac cycle 412, the motion waveform 405 has a first measured displacement as shown by horizontal dashed line 408. At the end 402 of the cardiac cycle 412, the motion waveform 405 has a second measured displacement as shown by horizontal dashed line 416. The difference in the displacements (relative to the vertical axis 410) of the motion waveform 405 at the start 401 and the end 402 of the cardiac cycle 412 indicates that the motion waveform 405 is non-periodic. A rotation technique may be applied to generate a rotated motion waveform 406 that is periodic, such as disclosed in U.S. application Ser. No. 14/328,513. The rotation technique shifts the PS motion data from the motion waveform 405 until defining the rotated motion waveform 406. The rotated waveform 406 has a common measured displacement at the start 401 and end 402 of the cardiac cycle 412. The common measured displacement corresponds to dashed line 408.

Additionally or alternatively, the navigation system 120 may average the PS motion data that corresponds to a map point (e.g., the map point 308) measured over a plurality of cardiac cycles to determine an average motion waveform for the map point. For example, the motion waveform may be combined through averaging or otherwise. Optionally, the PS motion data, which is utilized in connection with embodiments described hereafter, may include information indicative of a radial component of wall movement, and/or may include information indicative of a longitudinal component of wall movement. Optionally, the PS motion data may include information associated with 3-dimensional (3-D) movement calculated as a 3-D distance from an initial position at a select starting point in the cardiac cycle, such as an R-wave or local electrical activation time.

Returning to FIG. 2, at 204, the method designates anatomic landmarks by defining apical, basal, and circumferential landmarks within the point cloud data set. The anatomical landmarks may be designated through manual operations by the user. Additionally or alternatively, the anatomical landmarks may be designated through automatic calculations based on analysis of the point cloud data set, for example, as described in U.S. patent application Ser. No. 14/270,191, filed May 5, 2014, titled "METHOD AND SYSTEM TO AUTOMATICALLY ASSIGN MAP POINTS TO ANATOMICAL SEGMENTS", which is incorporated by reference in its entirety. The landmarks are located at various locations based upon the shape and nature of the region of interest. For example, at least one landmark is located proximate to, or at, the apex of the region of interest. Another landmark is located at, or proximate to, a middle of a base of the region of interest, while another landmark is located circumferentially from the base at an outer limit of the region of interest. For example, when the region of interest represents the right or left ventricle, the apex landmark represents the apex of the RV or LV. The basal landmark represents the base of the RV or LV and the circumferential landmark represents the left or right ventricular outflow tract.

One or more axes may be defined from the landmarks. For example, a long axis of the RV or LV is defined as a line connecting the apex to the basal point/landmark. A circumferential line is drawn from the basal landmark to the circumferential landmark. The long axis and circumferential line are used to position and orient a transformation coordinate system. For example, the long axis may be used as a Z-axis and the circumferential line is used as the circumferential line of the cylindrical coordinate system. The long axis and circumferential line are used as a basis to convert the point data from a base coordinate system, such as the Cartesian coordinate system, to a coordinate system associated with the regions of interest. For example, location coordinates for point data may be converted from XYZ Cartesian coordinates to longitudinal, radial and circumferential coordinates of the cylindrical coordinates.

At 206, the method 200 automatically calculates circumferential segment boundaries, within the point cloud data set, based on the apical, basal and circumferential landmarks.

At 208, the method 200 assigns map points to the circumferential segments as defined at 206. In order to automatically assign each map point, the method determines a corresponding segment of the anatomical map. To do so, in at least one embodiment, the method defines a reference line between the basal landmark and circumferential landmark. The circumferential location of each map point ($\theta m$) at a predefined point in the cardiac cycle, such as at the peak of the QRS complex, is compared against the circumferential landmark ($\theta LVOT$). A tolerance may be used such as ($\theta LVOT-\pi/6$—tolerance)$<\theta m \leq$($\theta LVOT+\pi/6$+tolerance). Each map point is assigned to the corresponding wall segment, where the circumferential landmark is used to identify a reference wall segment, such as the anteroseptal wall segment. Upon definition of the segment boundaries of the first wall segment, with the option of including a circumferential tolerance, the definitions of the other wall segments include the subsequent addition or subtraction of multiples of tolerance (e.g. $\pi/3$+tolerance) until the entire circumference of a region of interest (e.g, LV) is assigned to the appropriate wall segment.

Additionally or alternatively, the navigation system 120 may convert the map points from Cartesian coordinates to a cylindrical coordinate system (e.g., r, $\theta$, Z) when assigning the map points. Various techniques may be used for transforming between the Cartesian and cylindrical coordinate systems. Alternative base coordinate systems may be used instead of the Cartesian coordinate system. Optionally, the map points may be converted to an alternative coordinate system other than the cylindrical coordinate system. For example, the map points may be transformed to the spherical, polar or another system.

At 210, the method calculates longitudinal the segment boundaries. At 212, the method assigns map points to the segments based on the longitudinal segment boundaries. For example, the method performs segmentation along the long axis for definition of apical vs. mid-ventricular vs. basal points. The longest available length of the long axis ($L_{Long\ Axis}$) is determined. An apical portion (AP) parameter is then defined which determines the extent of the apical segments and $L_{Long\ Axis}$ is divided by AP, such that any point with a longitudinal coordinate less than $L_{Long\ Axis}/AP$ is assigned to the apex. A typical value for AP may be 3, in which the apical segments cover ⅓ of the length of the entire wall from apex to base. Next, the remaining points with longitudinal coordinates less than $$\frac{L_{LongAxis}(AP+1)}{2AP}$$

are assigned to the mid-ventricular segments and those with longitudinal coordinates more than this value are assigned to the basal segments. A longitudinal tolerance can also be introduced to allow for some flexibility in this assignment.

At 214, the map points are stored in a data storage with associated segment assignments. Additionally or alternatively, the navigation system 120 may calculate circumferential and longitudinal segment boundaries, for the point cloud data set, based on the apical, basal and circumferential landmarks as disclosed in U.S application Ser. No. 14/270, 191.

Figure 5:
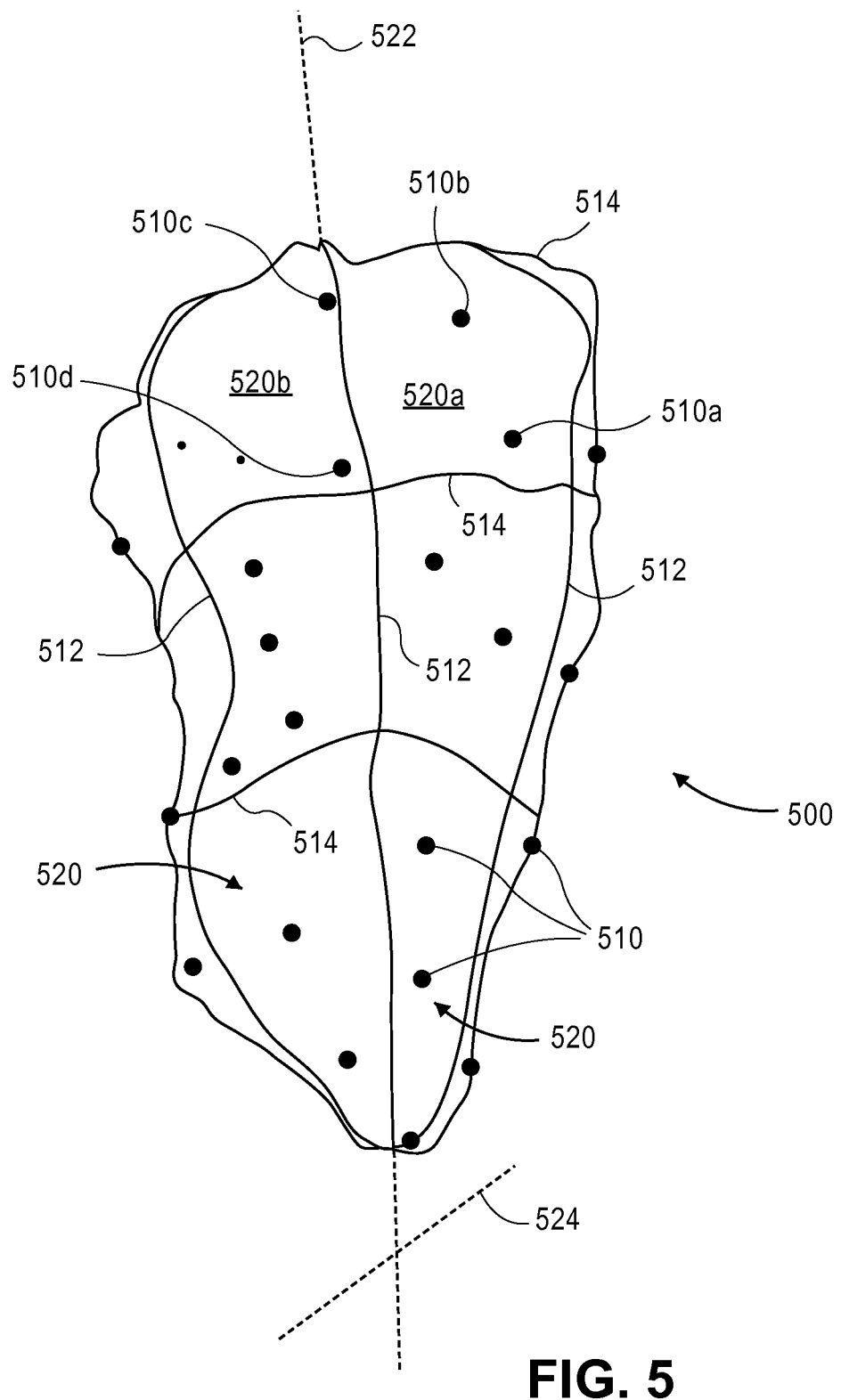
FIG. 5 illustrates map points within a segmented left ventricle in accordance with an embodiment herein.

FIG. 5 illustrates a three dimensional (3D) visualization of map points 510 located along the LV. The visualization 500 may be displayed on the display 158 in FIG. 1. FIG. 5 illustrates the left ventricular of the heart divided into segments 520 (not all segments shown) by circumferential segment boundaries 512 (not all boundaries are shown) and longitudinally segment boundaries 514 (not all boundaries are shown). It should be noted in alternative embodiments the number of circumferential and longitudinal segments may be fewer than or greater than shown in FIG. 5. Optionally, the three dimensional visualization 500 may include a graphical marker for an apical landmark, a basal landmark, and circumferential landmarks (e.g., septal, anterior-septal, anterior). The map points 510 are assigned to the segments in accordance with the operations at 208 and 210. In particular, as one example, the map points 510a-b are assigned to an associated segment 520a based on the location of the map points 510a-b, while map points 510c-d are assigned to the segment 520b.

Additionally or alternatively, the map points (as described above) may be based on a cylindrical coordinate system. For example, the map points 510 may be oriented based on a longitudinal axis 522, a polar or radial axis 524 with an origin approximate to the apex, and an angular coordinate or azimuth from the radial axis 524. It should be noted, in alternative embodiments the coordinate system may be oriented or have an origin on other landmarks within the region of interest, for example, the base, septal, or the like. Optionally, the coordinate system may be oriented or have an origin external to the region of interest (e.g., the heart), for example based on a reference external to the patient such as the transmitter assembly 150.

Optionally, a subset of the map points 510 may be assigned to multiple segments 520 based on the distance of the map points from at least one of the longitudinal and/or circumferential segment boundaries 512 and 514. For example, the map point 510d may be assigned to both the segments 520a and 520b based on the proximity to the circumferential segment boundary 512.

In accordance with some embodiments, the navigation system 120 may build a matrix (e.g., Matrix 1) based on the Cartesian coordinates of the map points within the segments and/or the wall, where $x_{11}$, $y_{11}$, and $z_{11}$ is the first x, y, and z position, respectively, at the first map point in the segment and/or the wall. Position $x_{12}$, $y_{12}$, $z_{12}$ is the second x, y, and z position, respectively, at the first map point in the segment and/or the wall position, $X_{1n}$, $y_{1n}$, $Z_{1n}$ is the $n^{th}$ x, y, and z position, respectively, at the first map point in the segment and/or wall. Position $x_{mn}$, $y_{mn}$, $z_{mn}$ is the $n^{th}$ x, y, and z position, respectively, at $m^{th}$ map point in the segment and/or the wall.

$$\begin{bmatrix} x_{11} & y_{11} & z_{11} \\ x_{12} & y_{12} & z_{12} \\ \ldots \\ x_{1n} & y_{1n} & z_{1n} \\ x_{21} & y_{21} & z_{21} \\ \ldots \\ \ldots \\ x_{mn} & y_{mn} & z_{mn} \end{bmatrix} \quad \text{(Matrix 1)}$$

The navigation system 120 may perform a factorization of the matrix (M) following Equation 1, where the variable U, of equation 1, is a unitary matrix, the variable S is a diagonal matrix containing singular values on the diagonal, and V* is a conjugate transpose of a unitary matrix V.

$$M = U \cdot S \cdot V^* \quad \text{(Equation 1)}$$

The navigation system 120 may create a new matrix, $S_k$, from the matrix S by maintaining a number of samples, k, representing the largest singular values within in the matrix S and setting the rest of the singular values to zero. Once the matrix $S_k$ is determined, the navigation system 120, may determine a new matrix $M_{filt}$ from Equation 2. Once $M_{filt}$ is determined, the navigation system 120 may separate $M_{filt}$ back into x, y, z and use the filtered x, y, z, data for further analysis.

$$Mf_{ilt} = U \cdot S_k \cdot V^* \quad \text{(Equation 2)}$$

Returning to FIG. 2, at 215, optionally, a 3D visualization 500 of the map points 510 is displayed (e.g. on the display 158 in FIG. 1) with associated segments 520.

At 216 the method 200 selects a region of interest from the point cloud data set. For example, the navigation system 120 may automatically, or the clinician (via the operator system interface 154) may manually, select a region of interest for further analysis in accordance with embodiments herein. By way of example, the user may use a mouse, curser and/or keyboard of the system interface 154 to "click on", draw around or otherwise designate the region of interest. The region of interest may be located within a segment, a plurality of segments, a portion of/entire apical region, a portion of/entire mid-ventricular region, a portion of/entire basal region, entire surface of the LV or RV, or the like.

At 218, the method 200 forms a triangulation area that includes a set of map points from the point cloud data set corresponding to the region of interest. The triangulation area corresponds to the region of interest. The triangulation area is defined by the set of map points within the region of interest. For example, the navigation system 120 may determine boundaries of the triangulation area based on positions of one or more of the select map points within the region of interest. The set of map points within the triangulation area may identify the map points to be used by the navigation system 120 to form one or more triangles as described at 220.

Figure 6:
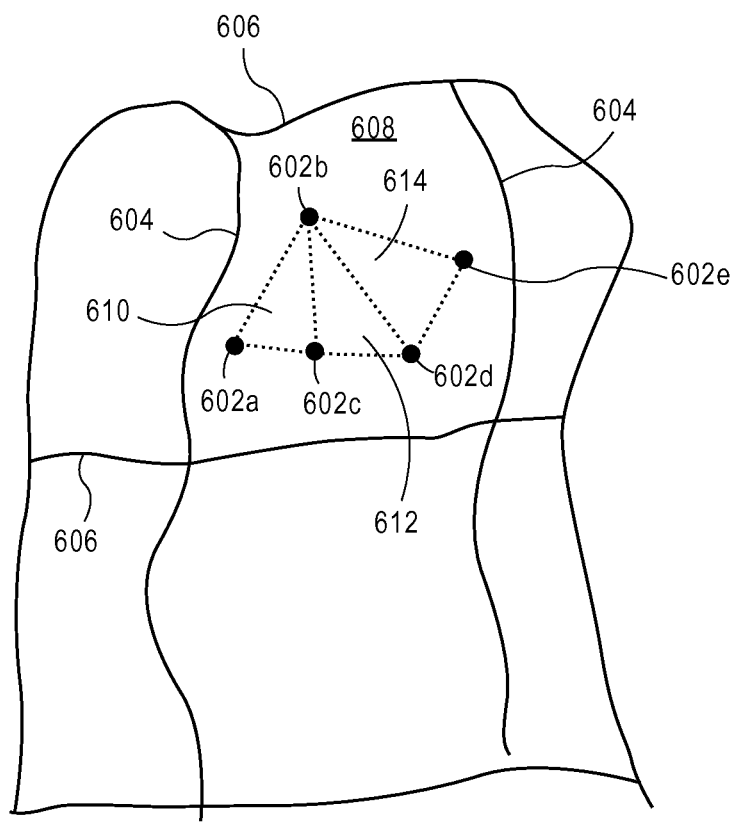
FIG. 6 illustrates a sub-divided region of interest within a three dimensional (3D) visualization of map points from a point cloud data set of the LV, in accordance with an embodiment disclosed herein.

At 220, the method 200 uses a triangulation technique, such as the DeLaunay triangulation algorithm, to generate at least one triangle within the triangulation area formed from at least a portion of the set of map points. For example, attention is directed to FIG. 6 to further discuss the operation at 220. FIG. 6 illustrates a visualization 600 of a set of map points. In the example of FIG. 6, the user has selected a region of interest within the segment 608. The segment 608 is bounded by circumferential segment boundaries 608 and longitudinal segment boundaries 604. It should be noted, although the region of interest is shown as the segment 608 in FIG. 6, the region of interest may be within a segment, a plurality of segments, a portion of/entire apical region, a portion of/entire mid-ventricular region, a portion of/entire basal region, entire surface of the LV or RV, or the like.

The navigation system 120 may apply a triangulation technique algorithm (TTA) (e.g., DeLaunay triangulation algorithm) to generate non-overlapping triangles 610-614 within a triangulation area corresponding to the region of interest (e.g., the segment 608). The TTA may maximize the minimum angle of the triangles to avoid skinny triangles. Each of the non-overlapping triangles 610-614 are formed from map points 602a-e within the segment 608. For example, the triangle 610 is formed from map points 602a-c. It should be noted that non-overlapping or overlapping triangles may be generated by the navigation system 120 using the TTA as further disclosed in U.S. Provisional Application 61/988,767, titled "METHOD AND SYSTEM TO SUBDIVIDE A MAPPING AREA FOR MECHANICAL ACTIVATION ANALYSIS", which is expressly incorporated herein in its entirety.

The navigation system 120 may determine and equalize cycle lengths (CL) of the x, y, z ensemble average data at the three triangle vertices (A,B,C) as disclosed in U.S. Provisional Application 61/988,763, titled "METHOD AND SYSTEM TO EQUALIZING CARDIAC CYCLE LENGTH BETWEEN MAP POINTS", which is expressly incorporated herein by reference in its entirety. From the ensemble average data, the navigation system 120 may calculate the three distances between the three vertices of triangles in 3-D space and determine an area of each triangle from equations 3 and 4 below. For example, the triangle 610 is formed from the vertices or map points 602a-c represented as A, B, and C respectively in Equations 3 and 4 below.

$$p = \frac{AB + AC + BC}{2} \quad \text{(Equation 3)}$$

$$A = \sqrt{p(p - AB)(p - AC)(p - BC)} \quad \text{(Equation 4)}$$

The navigation system 120 may determine the distance between the map points 602a-b, 602b-c, and 602a,c shown as variables AB, BC, and AC, respectively. From the distance between the map points 602a-c, the navigation system may determine the area of the triangle 610 using the equations 3 and 4. The navigation system 120 may further determine the area of the triangles 610-614 within the region of interest (e.g., the segment 608) to determine an area strain for each triangle 610-614.

The area strain ($\varepsilon_A$) of the triangles 610-614 over the cardiac cycle may be determined using Equation 5 below.

$$\varepsilon_A = \frac{A - A_o}{A_o} \quad \text{(Equation 5)}$$

Optionally, the navigation system 120 may define an area strain curve of each triangle 610-614 dependent on time. The variable A of Equation 5 represents an instantaneous area of the triangle 610-614 at a moment of time during the cardiac cycle. The variable $A_o$ of Equation 5 represents an initial area of the tissue in the triangle at some pre-defined temporal reference or time during the cardiac cycle. For example, the pre-defined temporal reference may be a time corresponding to a peak of the surface ECG R-wave.

Figure 9:
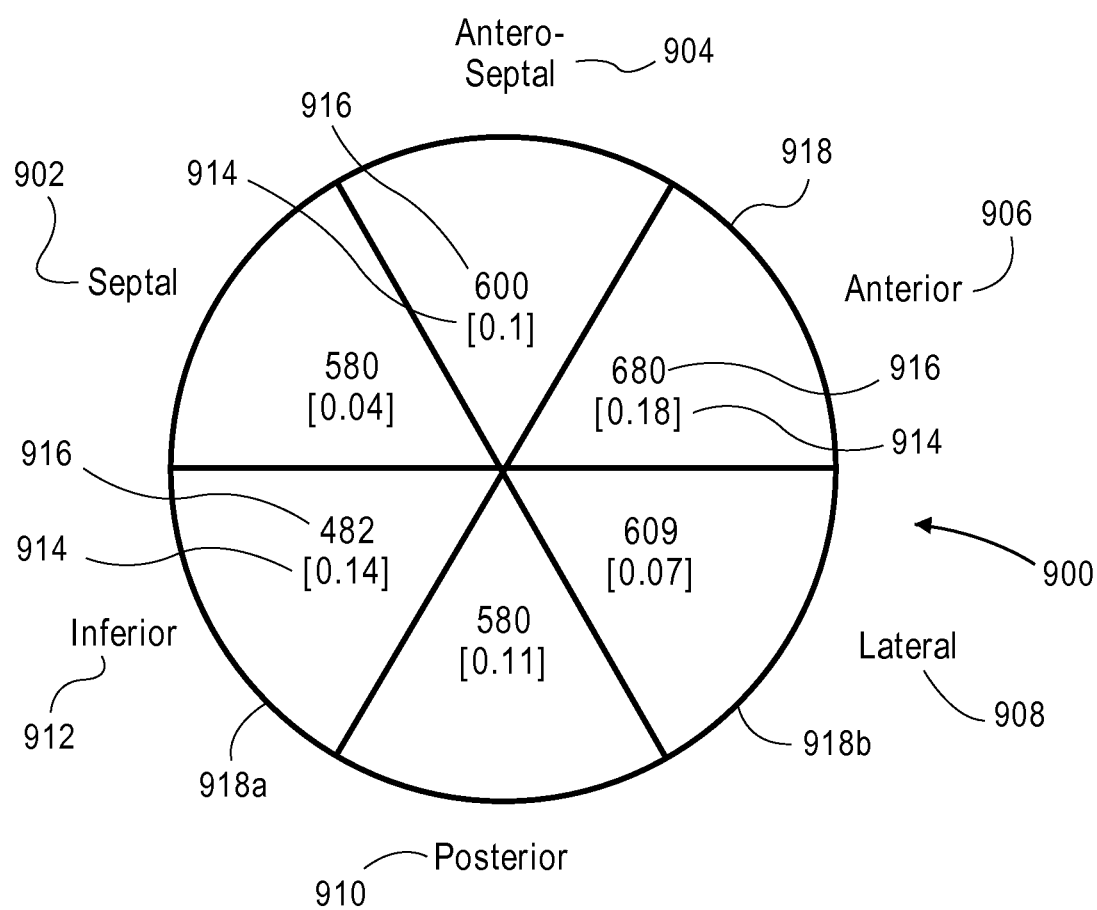
FIG. 9 illustrates a bullseye plot that summarizes the MAT determined from FIG. 8 for each wall, in accordance with an embodiment disclosed herein.
Figure 10:
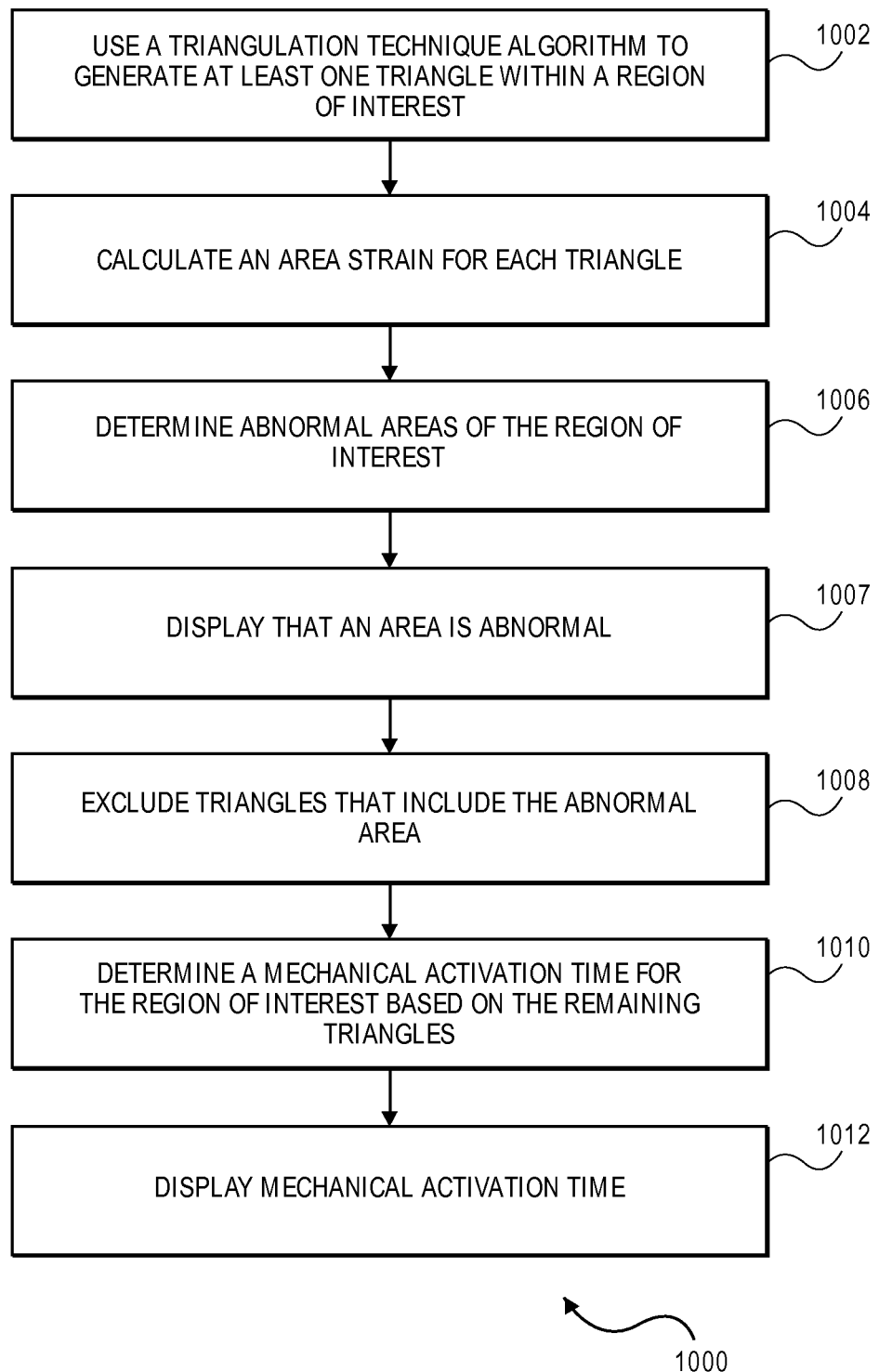
FIG. 10 illustrates a flow chart for determining the mechanical activation of a region of interest, in accordance with an embodiment disclosed herein.

FIG. 10 illustrates operations of a method 1000 that are further illustrated in connection with FIGS. 7-9. The method 1000 may be used to determine the mechanical activation of a region of interest. The method 1000, for example, may employ structures or aspects of various embodiments (e.g., systems and/or methods) discussed herein (e.g., the CNS 110 in FIG. 1). In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. It should be noted, other methods may be used, in accordance with an embodiment herein.

At 1002, the method 1000 uses a triangulation technique algorithm (TTA) to generate at least one triangle within a region of interest as explained in connection with FIG. 2.

At 1004, the method 1000 calculates an area strain for each triangle. For example, as described above from equation 5 and as described below in relation to FIG. 7. For example, the calculating operation may include calculating cycle lengths associated with map points corresponding to vertices of a first geometric area, calculating distances between the vertices, determining an area of the geometric area based on the distances between the map points corresponding to the vertices, and determining the area strain of the geometric area over at least one cardiac cycle.

At 1006, the method 1000 determines one or more abnormal areas within the region of interest. The geometric areas that are separate and distinct from the abnormal geometric areas represent valid geometric areas utilized when determining the mechanical activation time.

Optionally, at 1007, the method 1000 may display (e.g. on the display 158 in FIG. 1) that an area is abnormal.

At 1008, the method 1000 excludes triangle that include the abnormal area(s). At 1010, the method 1000 determines a mechanical activation time for the region of interest based on the remaining triangles as described in connection with FIGS. 7-9. By way of example, the excluding operation excludes map points based on at least one of a morphology of the geometric area, a presence of sharp spikes in the area strain associated with the corresponding geometric area, a size of the geometric area, a variability of cycle length within the geometric area or variation in electrical tissue characteristics associated with the geometric area. Optionally, at 1012, the method 1000 displays the activation time, for example, on the display 158 shown in FIG. 1.

Figure 7:
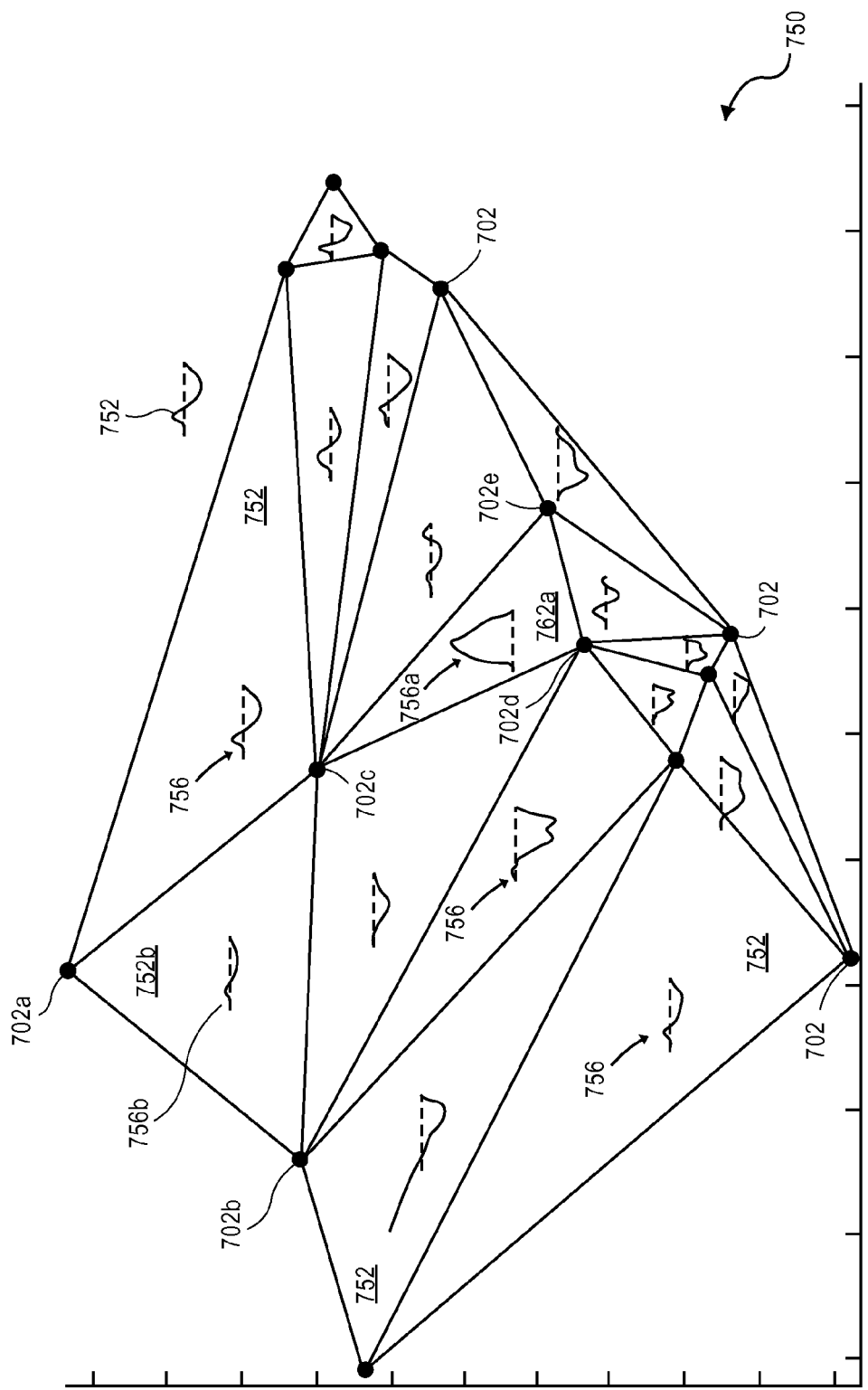
FIG. 7 illustrates a segment selected as a region of interest that is subdivided or segment divided into triangles, in accordance with an embodiment disclosed herein.

FIG. 7 illustrates a segment 750 selected as a region of interest that is subdivided or segment divided into triangles 752. The segment 750 maybe presented on the display 158. The triangles 752 are shown on the display 158 in 2D space formed by map points 702 using the TTA as described above at 1002. Each triangle 752 includes a corresponding area strain curve 756 calculated by the navigation system 120 as described above at 1004 in FIG. 10 and displayed on display 158. Optionally, the navigation system 120 may use a graphical marker or color, whether an area strain curve 756 is included in the MAT analysis (e.g., blue) or excluded (e.g., magenta).

The determination of the abnormal area(s) at 1006 may be performed in several manners. For example, the navigation system 120 may exclude one or more of the triangles used to determine the mechanical activation time (MAT) based on the morphology of the triangle, the presence of sharp spikes, the size of the triangle, the variability of the CL, and/or variation in electrical tissue characteristics as described further below. The triangles that are not excluded represent valid or included triangles and are associated with normal tissue areas.

Abnormal areas may be based on morphology because the morphology of a triangle may be unusual due to issues with acquiring the PS motion data at one or more vertices forming the triangle. Data issues include poor catheter contact, catheter slippage, and other such procedural inconsistencies. Morphology of each triangle can be evaluated by finding a correlation coefficient between the area strain curve of the triangle being evaluated and a template chosen at the beginning of the analysis process. If the correlation coefficient is below some predetermined threshold (e.g. 0.7), the triangle is excluded from analysis as an abnormal area.

Alternatively or in addition, abnormal areas may be based on the peaks of the area strain curve. The navigation system 120 may determine a number of local peaks of the area strain curve. If the number of peaks exceed a threshold such as, for example three, the morphology of the triangle may be considered abnormal and the triangle may be excluded by the navigation system 120 for determining MAT.

Presence of sharp spikes within the area strain curve may indicate some electrical or mechanical interference during the data collection of the PS motion data. A spike may be determined by the navigation system 120 as having a slope above a predetermined threshold. Optionally, the navigation system 120 may determine whether a spike is present by finding a second time derivative of the area strain curve, dividing the resulting curve by the difference between a maximum and minimum of the curve (e.g., peak to peak value), measuring the area under the resulting curve, and comparing the area of the curve against a predetermined threshold. If a spike is detected in the area strain curve, the triangle with the corresponding area strain curve may be excluded from the MAT analysis.

A triangle having an area below a set threshold may be excluded from MAT analysis as an abnormal area. The area of the triangle may correspond to the distance between the vertices or map points that form the triangle. If a triangle area is too small, then the behavior of such a triangle may not be representative of the contractile patterns. Triangles with areas below some predetermined threshold (e.g. 1 square millimeter), as measured at a reference time such as, for example, the R-wave on the ECG, may be excluded from further MAT analysis as abnormal areas.

Abnormal areas may be identified based on variability of the CL. The CL can vary greatly during the duration of data collection due to factors such as sedation and drug administration during the mapping procedure. Even though CLs are equalized earlier in the data analysis process, if a triangle combines points whose original CLs were vastly different, the area strain curve may be affected. The navigation system 120 may compare the data of the original CLs, prior to equalization, at each triangle vertex. Triangles with a difference between the shortest CL and the longest CL of more than a select threshold (e.g. 100 millisecond) may be excluded by the navigation system 120 from further MAT analysis.

The region of interest may include or be a portion of a heart chamber. The heart chamber may include areas of scarring or exhibiting low activity, which are likely to exhibit different types of movement or variable electrical tissue characteristics than areas without scarring or low electrical activity. Optionally, the navigation system 120 may adjust the TTA or manually combine map points that cover similar types of tissue into avoidance triangles. Additionally or alternatively, the area of the avoidance triangles may include border zones because the contractile patterns of such triangles may not be meaningful. The navigation system 120 may measure the voltage of the triangles or at the map points forming the triangles. In a triangle where some map points have a voltage below a certain threshold (e.g. 0.5 V) and some map points in the triangle have a voltage above that threshold, the triangle should be excluded from further analysis.

Additionally or alternatively, the navigation system 120 may measure conduction velocity between the map points forming the triangle. If there is large variability (e.g. >1.5 m/sec) between the conduction velocities, it may be an indication of mixed tissue characteristics and the navigation system 120 may exclude the triangle from further MAT analysis as an abnormal area.

Additionally or alternatively, triangles may be excluded from further MAT analysis for having an area under the curve that is larger than a select size. Preferably, normally-contracting myocardium involves the areas of the triangles decreasing as the heart squeezes inward with the area strain curve decreasing during the cardiac cycle. If the area strain curve increases during the cardiac cycle, the area under the curve will be positive and large. This type of behavior can be indicative of an area of dyskinesia, abnormal heart movement, or errors with data collection. Therefore, if the area under the area strain curve exceeds some threshold (e.g. 10 square millimeters), the triangle may be excluded from further MAT analysis as an abnormal area. Optionally, the navigation system 120 may indicate or note to the clinician via the display 158 that the triangle may be dyskinetic or otherwise an abnormal area.

For example, returning to FIG. 7, the triangle 752a formed from the map points 702c-e has a calculated area strain curve 756a. The navigation system 120 may determine that the area under the strain curve 756a exceeds a predetermined threshold and represents a dyskinesia, abnormal heart movement, or errors with data collection. The navigation system 120 may exclude the triangle 752a from the MAT analysis as an abnormal area. Further, the navigation system 120 may change the graphical marker or color (e.g., from blue to magenta) of the triangle 752a or the area strain curve 756a to indicate that the triangle 752a is excluded from further MAT analysis. Optionally, the navigation system 120 may determine if any of the triangle vertices also have a voltage below a certain threshold (0.5 V), to confirm dyskinesia. If the triangle vertices do not, the triangle may be excluded from analysis as an abnormal area by the navigation system 120 for further MAT analysis, but not considered dyskinetic.

As explained above, the preferable behavior of the area strain curve in healthy tissue is to decrease beyond some threshold and then return to a baseline. If the area strain curve does not increase as described above, but also does not decrease substantially, this area may be classified as hypokinetic, or exhibiting little movement. If the area strain curve does not reach a certain predetermined minimum threshold (e.g., such as −0.1), the triangle may be excluded from further analysis and the area of this triangle can be noted as being hypokinetic.

For example, the triangle 752b formed from the map points 702a-c has a calculated area strain curve 756b. The navigation system 120 may determine that the area strain curve 756b does not reach a certain predetermined minimum threshold. The navigation system 120 may exclude the triangle 752b from the MAT analysis as an abnormal area. Further, the navigation system 120 may change the graphical marker or color (e.g., from blue to magenta) of the triangle 752b or the area strain curve 756b to indicate that the triangle 752b is excluded from further MAT analysis.

For both dyskinesia and hypokinesia, certain portions of the heart, such as the septum or the LV outflow tract, may be prone to exhibiting less movement or inverse movement. Optionally, if the navigation system 120 determines that triangles fall into these areas, the navigation system 120 may adjust the thresholds corresponding to the triangles to determine whether the tissue within the triangle is dyskinetic or hypokinetic.

The triangles that are not excluded correspond to normal areas also referred to as included or valid triangles. Once the abnormal triangles have been excluded by the navigation system 120 as described above, the remaining included triangles may be combined to find the MAT for region of interest. The mechanical activation may be the time when the area strain curve begins to decrease (activation onset), the time when the area strain curve reaches its minimum or some percentage of its minimum or the like. One algorithm for finding the activation onset is to find when the second multipoint time derivative of the area strain curve reaches its minimum.

The time of mechanical activation may be found for each individual triangle based on the area strain curve. Optionally, the times may be combined together into the time of mechanical activation of the region containing the triangles. This may be done by taking a weighted or regular average of the individual triangle times of mechanical activation. The weights may be proportional to the area of the triangle, such that if the total area of a region, found by adding the areas of all the triangles in that region at some reference time point is $A_{TOTAL}$ and the area of the triangle being analyzed is $A_{TRIANGLE}$ at the same reference time point, the weight this triangle is assigned equals $A_{TRIANGLE}/A_{TOTAL}$.

Additionally or alternatively, after the triangles have equalized CL, the individual triangle area curves may be summed together, converted to the area strain curve, and the time of mechanical activation may be found for the entire sum.

Optionally, a percentage of area that is dyskinetic, hypokinetic, or simply excluded for earlier noted reasons may be calculated for each region of interest by dividing the sums of the dyskinetic, hypokinetic, or excluded triangle areas by the total area of the region (sum of all triangle areas in the region).

Figure 8:
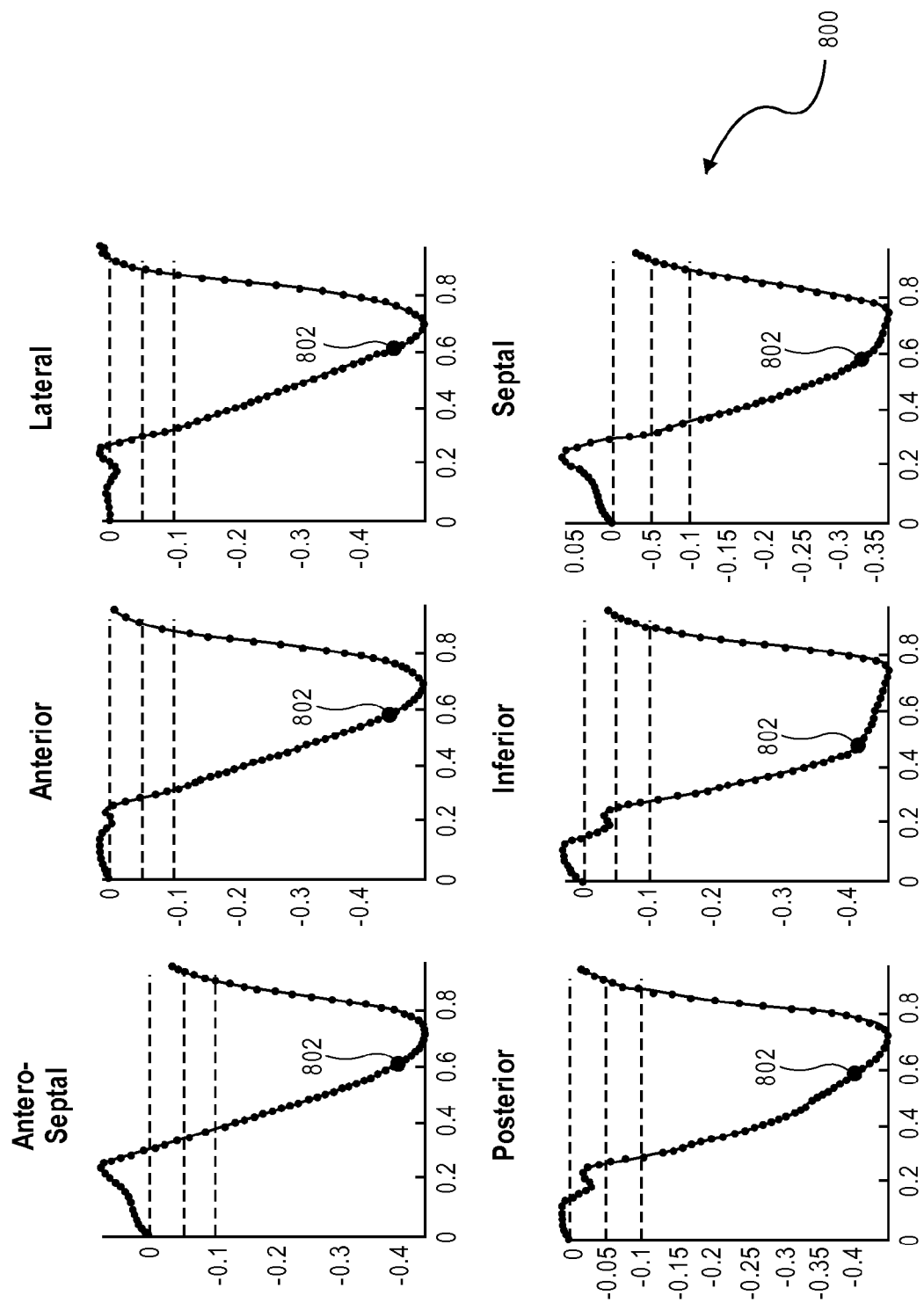
FIG. 8 illustrates the overall area strain curves for walls of a region of interest, in accordance with an embodiment disclosed herein.

FIG. 8 illustrates the overall area strain curves 800 for walls (e.g., antero-septal, anterior, lateral, posterior, inferior, septal) of the region of interest. The overall area strain curves 800 were formed by summing the area strain curves of the remaining triangles (e.g., 752) (triangle not excluded by the navigation system 120) for each wall. The MAT or time of mechanical activation 802 is indicated on each of the overall area strain curves 800. For example, the navigation system 120 determined that the MAT 802 occurs when the overall area strain curve 800 reaches 90% of the minimum. It should be noted, in embodiments the MAT 802 may be determined higher or below 90%.

FIG. 9 illustrates a bullseye plot 900 that summarizes the MAT 802 determined from FIG. 8 for each wall 902-912, which may be generated by the navigation system 120 on the display 158 at 1012 of FIG. 10. A number 916 represents the MAT 802 for the corresponding wall 902-912. A bracket number 914 indicates the percentage of the area of the wall 902-912 that is excluded from the MAT analysis. For example, the MAT of the inferior wall 912 was determined to occur at 482 milliseconds, and 14% of the area of the inferior wall 912 was excluded from the MAT analysis. Optionally, the bulls-eye plot 900 may be color coded 918 indicating a time continuum shift. For example, red 918a may indicate the earliest activating segment and/or wall and purple 918b the latest activating segment and/or wall.

Figure 11:
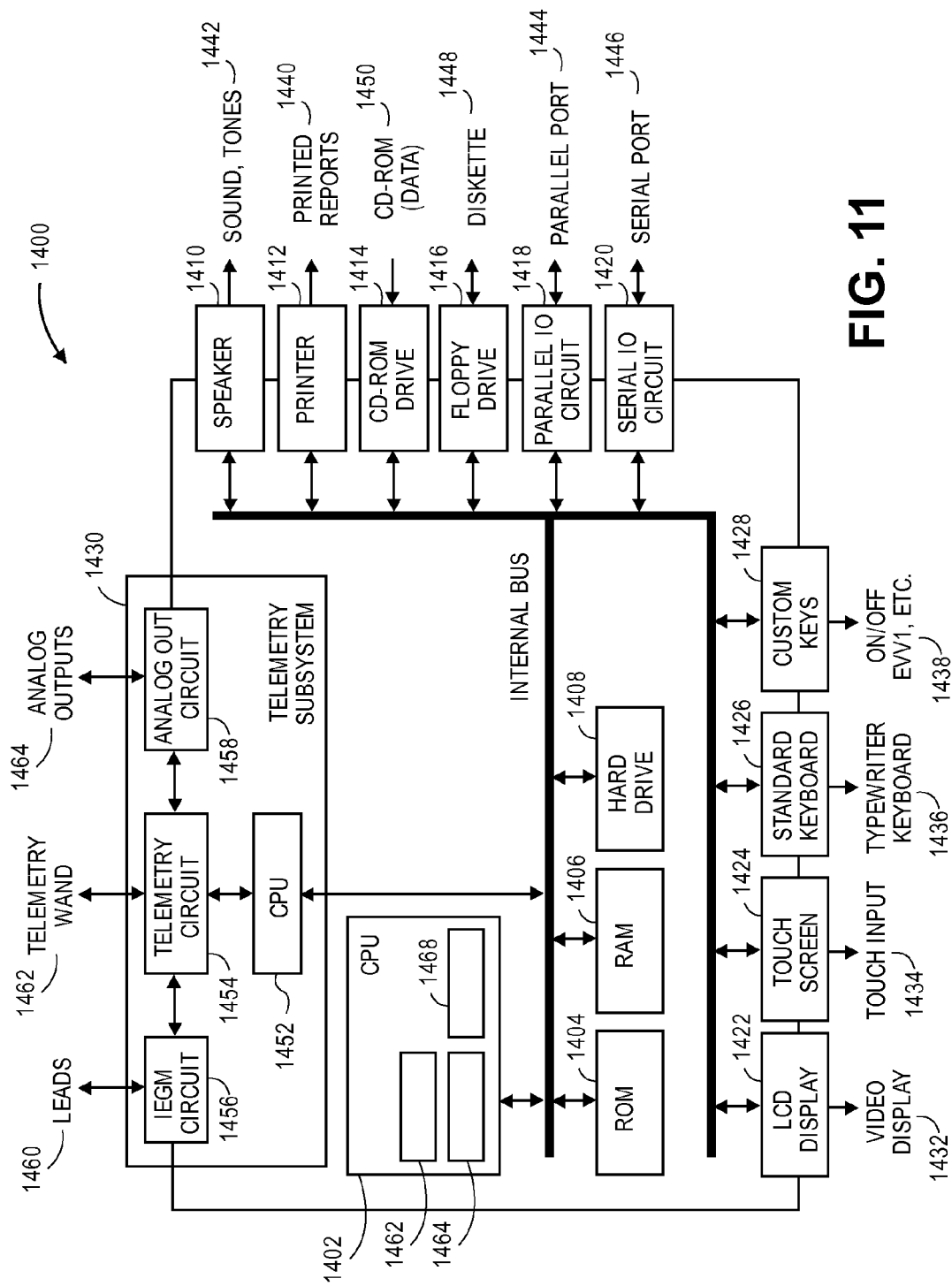
FIG. 11 illustrates a system for analyzing motion data in accordance with an embodiment.

FIG. 11 illustrates a functional block diagram of an embodiment of an electronic control unit (ECU) 1400 that is operated in accordance with the processes described herein to analyze motion data and to interface with the CNS 110. The ECU 1400 may be a workstation, a portable computer, a PDA, a cell phone and the like. The ECU 1400 includes an internal bus that connects/interfaces with a Central Processing Unit (CPU) 1402, ROM 1404, RAM 1406, a hard drive 1408, the speaker 1410, a printer 1412, a CD-ROM drive 1414, a floppy drive 1416, a parallel I/O circuit 1418, a serial I/O circuit 1420, the display 1422, a touch screen 1424, a standard keyboard connection 1426, custom keys 1428, and a telemetry subsystem 1430. The internal bus is an address/data bus that transfers information between the various components described herein. The hard drive 1408 may store operational programs as well as data, such as waveform templates and detection thresholds.

The CPU 1402 typically includes a microprocessor, a micro-controller, or equivalent control circuitry, and may interface with the CNS 110. The CPU 1402 may include RAM or ROM memory, logic and timing circuitry, state machine circuitry, and I/O circuitry to interface with the CNS 110. The display 1422 (e.g., may be connected to the video display 1432). The touch screen 1424 may display graphic information relating to the CNS 110. The display 1422 displays various information related to the processes described herein. The touch screen 1424 accepts a user's touch input 1434 when selections are made. The keyboard 1426 (e.g., a typewriter keyboard 1436) allows the user to enter data to the displayed fields, as well as interface with the telemetry subsystem 1430. Furthermore, custom keys 1428 turn on/off 1438 (e.g., EVVI) the ECU 1400. The printer 1412 prints copies of reports 1440 for a physician to review or to be placed in a patient file, and speaker 1410 provides an audible warning (e.g., sounds and tones 1442) to the user. The parallel I/O circuit 1418 interfaces with a parallel port 1444. The serial I/O circuit 1420 interfaces with a serial port 1446. The floppy drive 1416 accepts diskettes 1448. Optionally, the floppy drive 1416 may include a USB port or other interface capable of communicating with a USB device such as a memory stick. The CD-ROM drive 1414 accepts CD ROMs 1450.

The CPU 1402 is configured to analyze PS motion data collected by the CNS 110 for a plurality of map points to determine a point cloud data set of the map points stored on data storage (e.g., ROM 1404, RAM 1406, hard drive 1408). The CPU 1402 includes a segmentation analysis circuit module 1464 that is configured to automatically assign segment identifiers (IDs), which are associated with segments of the heart separated by circumferential and longitudinal boundaries, to the map points based on a position of the map point from the point cloud data set. The CPU 1402 also includes a position waveform generation circuit module 1462 that may generate position waveforms of selected reference locations based a coordinate system (e.g., Cartesian coordinate system, cylindrical coordinate system, or the like) as described herein. The CPU 1402 also includes a strain analysis circuit module 1468 that may determine the strain (e.g., linear or longitudinal strain, radial strain, circumferential strain), as explained herein.

The telemetry subsystem 1430 includes a central processing unit (CPU) 1452 in electrical communication with a telemetry circuit 1454, which communicates with both an IEGM circuit 1456 and an analog out circuit 1458. The circuit 1456 may be connected to leads 1460. The circuit 1456 may also be connected to implantable leads to receive and process IEGM cardiac signals. Optionally, the IEGM cardiac signals sensed by the leads may be collected by the CNS 110 and then transmitted, to the ECU 1400, wirelessly to the telemetry subsystem 1430 input.

The telemetry circuit 1454 is connected to a telemetry wand 1462. The analog out circuit 1458 includes communication circuits to communicate with analog outputs 1464. The ECU 1400 may wirelessly communicate with the CNS 110 and utilize protocols, such as Bluetooth, GSM, infrared wireless LANs, HIPERLAN, 3G, satellite, as well as circuit and packet data protocols, and the like. Alternatively, a hard-wired connection may be used to connect the ECU 1400 to the CNS 110.

It should be noted that although the above embodiments may focus on strain calculations in the LV, it should be understood, by one in the art, that the above described techniques may also be applied to other chambers and other organs in which local biomechanical behavior is interest. Additionally, it should be noted that although the above embodiments may focus on longitudinal strain, it should be understood by one in the art that the above described techniques may also be applies to radial positioned from endocardial and epicardial map points across the myocardial wall to obtain radial strain which is indicative of wall thickening. Similarly, circumferential positions can be used to obtain a measure of active twist during contraction.

One or more of the operations described above in connection with the methods (e.g. the method 200, the method 1000) may be performed and/or executed using one or more processors. The different devices in the systems described herein may represent one or more processors, and two or more of these devices may include at least one of the same processors. In one embodiment, the one or more operations described herein in connection to the method 200 and/or the method 1000 may represent actions performed when one or more processors (e.g., of the devices described herein) are hardwired to perform the methods or portions of the methods described herein, and/or when the processors (e.g., of the devices described herein) operate according to one or more software programs that are written by one or more persons of ordinary skill in the art to perform the operations described in connection with the methods.

The methods herein may be implemented as a software algorithm, package, or system that directs one or more hardware circuits or circuitry to perform the actions described herein. For example, the operations of the methods herein may represent actions to be performed by one or more circuits that include or are connected with processors, microprocessors, controllers, microcontrollers, Application Specific Integrated Circuits (ASICs), Field-Programmable Gate Arrays (FPGAs), or other logic-based devices that operate using instructions stored on a tangible and non-transitory computer readable medium (e.g., a computer hard drive, ROM, RAM, EEPROM, flash drive, or the like), such as software, and/or that operate based on instructions that are hardwired into the logic of the.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose several embodiments of the inventive subject matter and also to enable a person of ordinary skill in the art to practice the embodiments of the inventive subject matter, including making and using any devices or systems and performing any incorporated methods. The patentable scope of the inventive subject matter is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The foregoing description of certain embodiments of the inventive subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, processors or memories) may be implemented in a single piece of hardware (for example, a general purpose signal processor, microcontroller, random access memory, hard disk, and the like). Similarly, the programs may be stand-alone programs, may be incorporated as subroutines in an operating system, may be functions in an installed software package, and the like. The various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the inventive subject matter are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

In some embodiments, code including instructions (e.g., software, firmware, middleware, etc.) may be executed on one or more processing devices to implement one or more of the described functions or components. The code and associated components (e.g., data structures and other components used by the code or used to execute the code) may be stored in an appropriate data memory that is readable by a processing device (e.g., commonly referred to as a computer-readable medium).

The components and functions described herein may be connected or coupled in many different ways. The manner in which this is done may depend, in part, on whether and how the components are separated from the other components. In some embodiments some of the connections or couplings represented by the lead lines in the drawings may be in an integrated circuit, on a circuit board or implemented as discrete wires or in other ways.

What is claimed is:

1. A method for determining the mechanical activation of a region of interest, the method comprising:
    obtaining, using one or more processors, map point data associated with map points on a region of interest, the map point data representing at least one of motion or electrical activity data at the map points;
    assigning, using the one or more processors, the map points to non-overlapping geometric areas within the region of interest;
    calculating, using the one or more processors, an area strain for each geometric area based on the map point data for the map points of the associated geometric area;
    analyzing, using the one or more processors, a characteristic of the geometric areas to distinguish normal geometric areas from abnormal geometric areas based on whether the characteristic exhibits abnormal traits;
    excluding, using the one or more processors, map point data associated with the abnormal geometric area;
    determining, using the one or more processors, a mechanical activation time for the region of interest based on the map points for the normal geometric areas that were not excluded; and
    displaying the mechanical activation time for the region of interest.

2. The method of claim 1, wherein the abnormal areas are at least one of a hypokinetic area or dyskinetic area.

3. The method of claim 1, wherein the assigning operation generates the geometric areas as nonoverlapping triangular areas from at least a portion of the map points, where vertices of the triangular areas correspond to the map points.

4. The method of claim 1, wherein the geometric areas that are separate and distinct from the abnormal geometric areas represent valid geometric areas utilized when determining the mechanical activation time.

5. The method of claim 1, wherein the excluding operation marks the abnormal geometric areas as invalid geometric areas.

6. The method of claim 1, wherein the excluding operation excludes map points based on at least one of a morphology of the geometric area, a presence of sharp spikes in the area strain associated with the corresponding geometric area, a size of the geometric area, a variability of cycle length within the geometric area or variation in electrical tissue characteristics associated with the geometric area.

7. The method of claim 1, wherein the calculating operation includes calculating cycle lengths associated with map points corresponding to vertices of a first geometric area, calculating distances between the vertices, determining an area of the geometric area based on the distances between the map points corresponding to the vertices, and determining the area strain of the geometric area over at least one cardiac cycle.

8. A system comprising:
  a data storage configured to store map point data collected by an intravascular mapping tool configured to be inserted into at least one of the endocardial or epicardial space, the mapping tool maneuvered to select locations proximate to surfaces of the heart, while collecting the map point data at map points to form a point cloud data set during at least one cardiac cycle, the map point data representing at least one of motion or electrical activity data at the map points; and
  a processor configured to:
    assign the map points to non-overlapping geometric areas within the region of interest;
    calculate an area strain for each geometric area based on the map point data for the map points of the associated geometric area;
    analyze a characteristic of the geometric areas to distinguish normal geometric areas from abnormal geometric areas based on whether the characteristic exhibits abnormal traits;
    exclude the map point data associated with the abnormal geometric area;
    determine a mechanical activation time for the region of interest based on the map points for the normal geometric areas that were not excluded and display the mechanical activation for the region of interest.

9. The system of claim 8, wherein the abnormal areas are at least one of a hypokinetic area or dyskinetic area.

10. The system of claim 8, wherein the processor uses a triangulation technique algorithm to generate the geometric areas as nonoverlapping triangular areas from at least a portion of the map points, where vertices of the triangular areas correspond to the map points.

11. The system of claim 8, wherein the geometric areas that are separate and distinct from, the abnormal geometric areas represent valid geometric areas utilized when determining the mechanical activation time.

12. The system of claim 8, wherein the processor marks the abnormal geometric areas as invalid geometric areas.

13. The system of claim 8, wherein the processor excludes map points based on at least one of a morphology of the geometric area, a presence of sharp spikes in the area strain associated with the corresponding geometric area, a size of the geometric area, a variability of cycle length within the geometric area or variation in electrical tissue characteristics associated with the geometric area.

14. The system of claim 8, wherein the processor calculates cycle lengths associated with map points corresponding to vertices of a first geometric area, calculating distances between the vertices, determining an area of the geometric area based on the distances between the map points corresponding to the vertices, and determining the area strain of the geometric area over at least one cardiac cycle.

* * * * *